United States Patent [19]

Schwartz et al.

[11] Patent Number: 5,512,686

[45] Date of Patent: Apr. 30, 1996

[54] METHOD FOR THE PURIFICATION OF DIOXYDIPHTHALIC ANHYDRIDE AND ESTER INTERMEDIATE MADE THEREIN

[75] Inventors: Willis T. Schwartz, Grand Island; Frank J. Dinan, Tonawanda, both of N.Y.; Jeffrey S. Stults, West Lafayette, Ind.

[73] Assignee: Occidental Chemical Corporation, Niagara Falls, N.Y.

[21] Appl. No.: 414,827

[22] Filed: Mar. 31, 1995

[51] Int. Cl.⁶ .................... C07D 493/14; C07D 319/24
[52] U.S. Cl. .............................. 549/234; 549/359
[58] Field of Search ................... 549/234, 359

[56] References Cited

U.S. PATENT DOCUMENTS

| | | | |
|---|---|---|---|
| 3,356,691 | 12/1967 | Gaertner | 549/242 |
| 5,003,086 | 3/1991 | Stults et al. | 549/234 |
| 5,089,631 | 2/1992 | Stults et al. | 549/234 |
| 5,166,404 | 11/1992 | Stults et al. | 560/65 |

OTHER PUBLICATIONS

Schwartz et. al., High Performance Polymers, vol. 6, No. 2, pp. 155–163 (1994).
Indian Journal of Chemistry, Govindachari et al, vol. 5, Mar. 1967.

*Primary Examiner*—Bernard Dentz
*Attorney, Agent, or Firm*—Wayne A. Jones; Arthur S. Cookfair

[57] ABSTRACT

Crude mixtures of dioxydiphthalic anhydride containing alkali metal salts are purified by treating the crude mixture with an alkanol, such as n-butanol, to form the dioxydiphthalic acid diester; removing the insoluble alkali metal salts by filtration; removing the excess alkanol; and reconverting the dioxydiphthalic acid diester to dioxydiphthalic anhydride.

13 Claims, No Drawings

METHOD FOR THE PURIFICATION OF DIOXYDIPHTHALIC ANHYDRIDE AND ESTER INTERMEDIATE MADE THEREIN

BACKGROUND OF THE INVENTION

1. Field of the Invention

This invention relates to a method for the purification of dioxydiphthalic anhydrides and to novel dioxydiphthalic esters useful in the purification method. Dioxydiphthalic anhydride is useful in the preparation of polyimides in a known manner by polycondensation with a suitable diamine.

2. Prior Art

Polyimides prepared from dioxydiphthalic anhydrides are useful in various industrial applications, particularly in the electronics field where purity of the polyimide is of paramount importance. In the production of dioxydiphthalic anhydride by methods known in the art (see for example, U.S. Pat. Nos. 5,089,631 and 5,003,086), a dihalophthalic anhydride of the formula

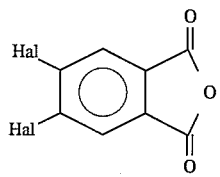

where Hal is F, Cl, Br, or I, is reacted with an alkali metal compound such as KF or $K_2CO_3$. The crude reaction product typically contains residual salts such as $K_2CO_3$ and KCl (or other alkali metal halides, depending on the particular dihalophthalic anhydride reactant employed).

Dioxydiphthalic acid may be characterized by the formula:

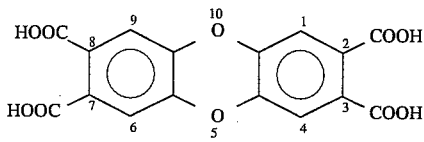

The preparation of dioxydiphthalic acid and the reaction thereof with diazomethane to yield the tetra-methyl ester is reported by Govindachari et al, in the Indian Journal of Chemistry, Vol. 5, March 1967.

U.S. Pat. No. 5,166,404 to Stults et al discloses the preparation of dioxydiphthalic acid esters by reaction of dioxydiphthalic anhydride with an alkanol.

U.S. Pat. No. 3,356,691 to Gaertner discloses a process for the purification of crude benzophenone tetracarboxylic dianhydride by treating with a low boiling alcohol to dissolve impurities and filtering the mixture to separate the alcohol containing dissolved impurities. The patentee teaches that alcohols may react with dianhydrides to produce acid esters. However, the patentee, whose invention is a process for purifying benzophenone dianhydride, notes that the formation of esters should be avoided.

PROBLEM TO BE SOLVED

In the manufacture of polyimides from dioxydiphthalic anhydride (DODA), the purity of the anhydride is of particular importance. The preparation of DODA from dihalophthalic anhydride, for example, as disclosed in U.S. Pat. Nos. 5,089,631 and 5,003,086, typically results in a crude reaction product containing residual salts such as $K_2CO_3$, KCl, and/or other alkali metal halides. The removal of impurities, such as residual salts, from the dianhydride reaction product is of particular importance where the dianhydride is to be employed in the preparation of high performance polyimides for electronics applications. The presence of impurities, in addition to causing a deterioration of electrical properties, will result in an offset in stoichioimetry during polyimide preparation, with a consequent lowering of molecular weight of the polyimide and a reduction of physical properties. The purification of DODA is difficult because of its extreme insolubility in a wide range of solvents and solvent blends that might normally be used for its recrystallization. Attempts to recrystallize DODA from the solvent in which it is formed, for example, sulfolane, have resulted in a re-precipitation with no improvement in purity. The purification method of the present invention is directed to the removal of impurities, including residual salts such as alkali metal salts, from dioxydiphthalic anhydride.

The present invention provides a simple and effective process for the purification of crude dioxydiphthalic anhydride.

SUMMARY OF THE INVENTION

It has now been found that crude mixtures of dioxydiphthalic anhydride, containing alkali metal salts such as potassium carbonate and potassium halides, may be treated and high purity dioxydiphthalic anhydride recovered by a process comprising 1) reacting the crude dioxydiphthalic anhydride with a $C_3$–$C_5$ alkanol to form the diester thereof;
2) separating insoluble alkali metal salts from the reaction mixture;
3) converting the diester back to the dianhydride form.

There are three possible isomeric alkyl diesters of dioxydiphthalic acid (2,3-, 2,7-, and 2,8- isomers). In the reaction set forth as step 1, above, the formation of the 2,3-diester (where both ester groups are on the same phthalic group) is inhibited and the 2,7- and 2,8- isomers are preferentially formed.

The 2,7- and 2,8- alkyl diesters of dioxydiphthalic acid, prepared as in step 1 of the above purification method, are novel compounds characterized by the formula:

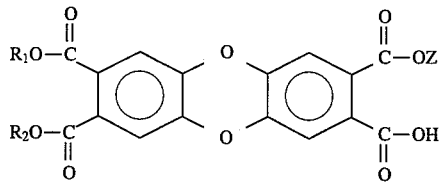

where Z is an alkyl of 3–5 carbon atoms and one of $R^1$ and $R^2$ is H and one of $R^1$ and $R^2$ is the same as Z. The preferred alkyl diesters of this invention are the 2,7-dibutylester, characterized by the formula:

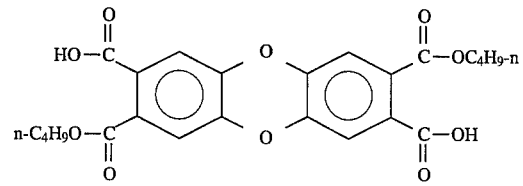

and the 2,8-dibutylester, of the formula:

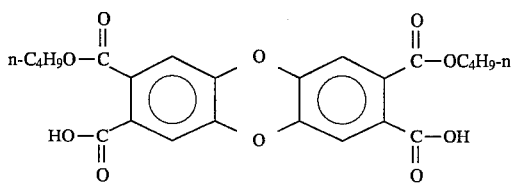

DETAILED DESCRIPTION OF THE INVENTION

The conversion of the dioxydiphthalic anhydride to the diester involves the treatment of the crude dianhydride mixture, containing residual salts and other impurities, with a suitable alkanol to form the corresponding diester by solvolysis reaction. The impurities to be removed remain insoluble and may be removed by physical separation means, e.g., filtration or centrifugation. The selection of alkanol is based to a great extent on its boiling point and solvent characteristics. Because of their lower boiling points, the lower alkanols, e.g., ethanol, tend to be less effective as solvents for the dioxydiphthalic anhydride and the diesters. On the other hand, the lower alkanols, e.g., ethanol are more polar and exhibit a greater tendency to dissolve polar impurities such as any acid present or any dioxydiphthalic acid salts formed. The higher alkanols, e.g., octanol, exhibit more desirable solvent characteristics but the residual alkanol is more difficult to remove completely from the reaction product. The preferred alkanols are $C_3$ to $C_5$ n-alkanols, and more preferably, n-butanol. Typically, the diester formation is carried out by adding a stoichiometric excess of the alcohol to the crude solid dianhydride mixture and heating the mixture to substantially dissolve the organic component and convert the dianhydride to a diester and dissolve the diester in the alcohol. The solvolysis reaction temperature is preferably about 70° Celsius or higher, and most preferably about 95° Celsius to the boiling point of the mixture. In a preferred mode, the reaction mixture is heated to reflux temperature and maintained thereat until the diester is formed and substantially all soluble materials are dissolved. The insoluble components, especially alkali metal salts, including for example, $K_2CO_3$, $Na_2CO_3$, NaCl, KCl, KBr, KF and the like, and other insolubles, e.g., dioxydiphthalic acid or acid salts may then be conveniently removed by physical separation means, such as filtration or centrifugation. For most effective removal of impurities, it is preferred to filter the reaction mixture at a temperature above the temperature at which the diester will precipitate, that is, typically at a temperature of above about 60° C. and most preferably about 100° C. to 120° C., depending on the ester/alcohol.

The reconversion of the diester to the dianhydride may be carried out either by thermal treatment, typically at temperature of above about 230° C., with loss of alkanol, or chemically by treatment with acetic anhydride.

The following examples are provided to further illustrate the invention and the manner in which it may be carried out. The specific details given in the examples have been chosen for purposes of illustration only and are not to be construed as limiting the invention.

EXAMPLE 1

Preparation of Dioxydiphthalic Anhydride

A solution of 21.7 grams (0.1 mole) of 4,5-dichlorophthalic anhydride in 40 grams of sulfolane was heated and maintained at 210°–215° C. while 0.215 grams of tetraphenylphosphonium bromide was added, followed by the incremental addition of 13.82 grams (0.1 mole) of potassium carbonate over a period of about 4 hours. The temperature was maintained an additional hour and the reaction mixture was then cooled to room temperature. Acetone (100 ml) was added and mixed. The reaction mixture was filtered and the solids washed consecutively with another 100 ml of acetone, two 100 ml portions of water, and again with 100 ml of acetone, to yield about 15 grams of brown solid. After drying, the solid was recrystallized from about 225 grams of 1,2,4-trichlorobenzene to yield 12.5 grams of a tan colored crystalline solid. Mass spectral analysis indicated the product to have a molecular weight of 324 with a fragmentation consistent with dioxydiphthalic anhydride. The identification of dioxydiphthalic anhydride was confirmed by infra-red analysis and $C^{13}$ NMR (CP/MAS).

EXAMPLE 2

Preparation of Dioxydiphthalic Anhydride 4,5-Difluorophthalic anhydride (18.4 grams, 0.1 mole) was dissolved in 40 grams of anhydrous sulfolane and heated to 165° C. with stirring. Tetraphenylphosphonium bromide (0.184 grams, 0.0004 mole) and 1.8 grams (0.10 mole) of water were added and the temperature increased to 200° C. Anhydrous potassium fluoride (23.3 grams, 0.4 mole) was added with stirring. The reaction mixture was held at about 200° C. with stirring for about 3½ hours at which time another 0.2 grams of water was added and the reaction mixture was maintained at temperature for an additional hour. The reaction mixture was cooled to less than 150° C. and 35 grams of acetone added and the solids filtered off. The solids were washed with acetone followed by three 100 ml washes with distilled water. The solid material was dried at 150° C. for 16 hours to yield 15.5 grams (95.7% yield) of dioxydiphthalic anhydride.

EXAMPLE 3

Preparation of the Di-n-butyl Ester of Dioxydiphthalic Acid and Removal of Impurities Dioxydiphthalic anhydride, prepared as in Example 1 (25.0 g, 0.77 mole) was added to 175 mL of dry 1-butanol. The mixture was heated to reflux and maintained thereat, with stirring, for about 16 hours. The reaction mixture was then filtered at about 110° C. and the alcohol-insoluble solids (12 g) discarded. The volume of the alcohol solution was then reduced under rotary evaporation until a pronounced cloudiness was observed. This saturated solution was then combined, at room temperature, with a large volume of n-hexane to induce crystallization. The solid product (dioxydiphthalic acid diester) was removed by filtration in vacuo, rinsed with hexane and dried to afford 29.6 g. of a mixture of the 2,7- and 2,8-dibutylesters of dioxydiphthalic acid (an 81.3% yield).

EXAMPLE 4

Preparation of Dioxydiphthalic Anhydride by Cyclization of the Di-n-butyl Esters A mixture of di-n-butyl ester isomers of dioxydiphthalic acid, 141 g, prepared as in Example 3, was added to 700 mL of acetic anhydride and heated to reflux under a nitrogen atmosphere. The diester isomers dissolved in the hot solvent to form a dark brown solution. The solution was refluxed overnight to allow complete precipitation of dioxydiphthalic anhydride from the solution. The solid product was filtered, washed with acetone and dried to afford 74.3 g (76.8% yield) of high purity dioxydiphthalic anhydride.

We claim:

1. A process for the purification of dioxydiphthalic anhydride which comprises
   (A) treating a crude mixture of dioxydiphthalic anhydride and alkali metal salts with an alkanol selected from $C_3$–$C_5$ alkanols, to form the dioxydiphthalic acid diester thereof, the alkanol being present in sufficient excess to dissolve the diester;
   (B) removing the insoluble alkali metal salts from the crude reaction product of step (A); and
   (C) converting the dioxydiphthalic acid diester to dioxydiphthalic anhydride.

2. A process according to claim 1 wherein the alkali metal salts are removed by filtration.

3. A process according to claim 2 wherein the alkali metal salts comprise potassium salts.

4. A process according to claim 3 wherein the potassium salts include one or more salts selected from the group consisting of $K_2CO_3$, KF, KCl, and KBr.

5. A process according to claim 4 wherein the filtration is carried out at a temperature of about 100° to 120° Celsius.

6. A process acording to claim 1 wherein the alkanol is n-butanol.

7. A process according to claim 6 wherein the alkali metal salts are selected from the group consisting of $K_2CO_3$, KF, KCl, and KBr.

8. A process according to claim 7 wherein the alkali metal salts are removed by filtration.

9. A process according to claim 8 wherein the filtration is carried out at a temperature of about 100° to 120° Celsius.

10. A process for the purification of a crude dioxydiphthalic anhydride mixture containing alkali metal salts which comprises:
    (A) treating a crude mixture of dioxydiphthalic anhydride and one or more potassium metal salts selected from the group consisting of potassium carbonate, potassium fluoride and potassium chloride, by reaction with n-butanol at a temperature of from about 70° Celsius to reflux temperature to form the n-butyl diester of dioxydiphthalic acid and dissolve the n-butyl diester to produce a crude reaction product comprising a solution of the n-butyl diester of dioxydiphthalic acid in admixture with insoluble potassium salts;
    (B) filtering the crude reaction product of step (A) at a temperature of 100° to 120° to remove the potassium salts; and
    (C) converting the n-butyl ester of dioxydiphthalic acid to dioxydiphthalic anhydride.

11. A dioxydiphthalic acid ester characterized by the formula:

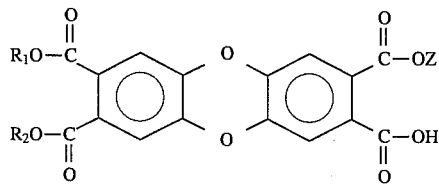

where Z is n-butyl, one of $R^1$ and $R^2$ is H and one of $R^1$ and $R^2$ is n-butyl.

12. A dioxydiphthalic acid ester according to claim 10 characterized by the formula:

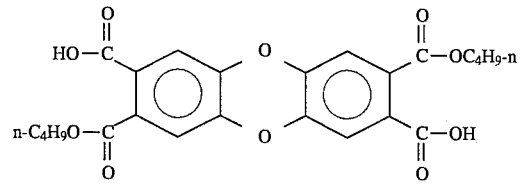

13. A dioxydiphthalic acid ester according to claim 10 characterized by the formula:

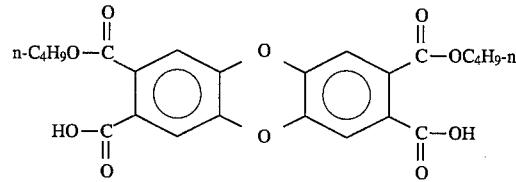

* * * * *